United States Patent
Toriyama et al.

(10) Patent No.: US 8,977,338 B2
(45) Date of Patent: Mar. 10, 2015

(54) BIOLOGICAL OPTICAL MEASUREMENT APPARATUS, MEASUREMENT PROBE, AND BIOLOGICAL OPTICAL MEASUREMENT SYSTEM

(71) Applicant: Olympus Medical Systems Corp., Tokyo (JP)

(72) Inventors: Seiki Toriyama, Tokyo (JP); Kazuhiro Gono, Sagamihara (JP); Seigo Ito, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/160,654

(22) Filed: Jan. 22, 2014

(65) Prior Publication Data
US 2014/0206934 A1 Jul. 24, 2014

Related U.S. Application Data

(63) Continuation of application No. PCT/JP2013/070063, filed on Jul. 24, 2013.

(60) Provisional application No. 61/682,425, filed on Aug. 13, 2012.

(51) Int. Cl.
*A61B 5/05* (2006.01)
*A61B 1/00* (2006.01)
*A61B 5/00* (2006.01)

(52) U.S. Cl.
CPC ........... *A61B 1/00057* (2013.01); *A61B 5/0059* (2013.01); *A61B 1/00147* (2013.01); *A61B 1/00121* (2013.01); *A61B 2562/228* (2013.01)
USPC ........... 600/407; 600/131; 600/132; 600/147; 600/476

(58) Field of Classification Search
USPC .......................... 600/407, 131, 132, 147, 476
See application file for complete search history.

(56) References Cited

U.S. PATENT DOCUMENTS

| | | | |
|---|---|---|---|
| 8,465,330 B2 * | 6/2013 | Miyagi et al. | 439/701 |
| 8,568,301 B2 * | 10/2013 | Watanabe et al. | 600/132 |
| 8,758,233 B2 * | 6/2014 | Masaki et al. | 600/147 |
| 2008/0281157 A1 | 11/2008 | Miyagi et al. | |
| 2010/0053632 A1 | 3/2010 | Alphonse et al. | |

FOREIGN PATENT DOCUMENTS

| | | |
|---|---|---|
| JP | A-2008-12099 | 1/2008 |
| JP | A-2008-278971 | 11/2008 |
| JP | A-2009-334 | 1/2009 |
| JP | A-2011-209425 | 10/2011 |

OTHER PUBLICATIONS

International Search Report issued in International Patent Application No. PCT/JP2013/070063 dated Oct. 29, 2013.

\* cited by examiner

*Primary Examiner* — Joel Lamprecht
(74) *Attorney, Agent, or Firm* — Oliff PLC

(57) ABSTRACT

A biological optical measurement apparatus includes a connector unit to which a measurement probe is detachably connected, a supply unit configured to supply air to the connector unit, a pipe that connects the connector unit and the supply unit, a pressure detection unit configured to detect a pressure value in the pipe, and an abrasion determination unit configured to determine abrasion of the connector unit based on the pressure value detected by the pressure detection unit under conditions that the measurement probe is connected to the connector unit.

6 Claims, 13 Drawing Sheets

BIOLOGICAL OPTICAL MEASUREMENT APPARATUS, MEASUREMENT PROBE, AND BIOLOGICAL OPTICAL MEASUREMENT SYSTEM

CROSS-REFERENCE TO RELATED APPLICATIONS

This application is a continuation of PCT international application Ser. No. PCT/JP2013/070063 filed on Jul. 24, 2013 which designates the United States, incorporated herein by reference, and which claims the benefit of priority from U.S. provisional application No. 61/682,425 filed on Aug. 13, 2012, incorporated herein by reference.

BACKGROUND OF THE INVENTION

1. Field of the Invention

The present invention relates to a biological optical measurement apparatus which measures optical characteristics of body tissue, a measurement probe connected to the biological optical measurement apparatus, and a biological optical measurement system.

2. Description of the Related Art

In recent years, a biological optical measurement apparatus is known which irradiates illumination light to body tissue and estimates the nature of the body tissue on the basis of measurement values of detected light reflected or scattered from the body tissue. The biological optical measurement apparatus is used in combination with an endoscope for observing an internal organ such as a digestive organ. As such a biological optical measurement apparatus, a biological optical measurement apparatus is proposed which uses LEBS (Low-Coherence Enhanced Backscattering Spectroscopy) that detects the nature of body tissue by irradiating low-coherence white light whose spatial coherence length is short from the tip of an illumination fiber of a measurement probe to the body tissue and measuring intensity distribution of scattering light of a plurality of angles by using a plurality of light receiving fibers (see US Patent Application Laid-open No. 2010/0053632).

The biological optical measurement apparatus and the measurement probe described above are optically connected to each other by using an SMA (Sub-Miniature Type A) connector. FIG. 13 is a cross-sectional view illustrating a state in which SMA connectors are used as connectors to connect a conventional biological optical measurement apparatus and a measurement probe. In a biological optical measurement apparatus 1000 illustrated in FIG. 13, a connector unit 1002 is fixed to a housing 1001 by a nut 1003. An SMA connector 1005 holding an optical fiber 1004 and an SMA connector 1006 holding an optical fiber 1004 are inserted into the connector unit 1002 from both ends of the connector unit 1002, respectively, and screwed and fixed to the connector unit 1002. Thereby, an end surface of the SMA connector 1005 and an end surface of the SMA connector 1006 come into contact with each other, so that both optical fibers 1004 are optically connected to each other.

SUMMARY OF THE INVENTION

A biological optical measurement apparatus according to one aspect of the invention is a biological optical measurement apparatus to which a measurement probe configured to be inserted into a subject is connected and which performs an optical measurement on body tissue. The biological optical measurement apparatus includes a connector unit to which the measurement probe is detachably connected, a supply unit configured to supply air to the connector unit, a pipe that connects the connector unit and the supply unit, a pressure detection unit configured to detect a pressure value in the pipe, and an abrasion determination unit configured to determine abrasion of the connector unit based on the pressure value detected by the pressure detection unit under conditions that the measurement probe is connected to the connector unit.

A measurement probe according to another aspect of the invention is a measurement probe detachably connected to a connector unit of a biological optical measurement apparatus which performs an optical measurement on body tissue. The measurement probe includes a holding member including a main body which has a cylindrical shape having the same diameter as an internal diameter of the connector unit and which is configured to be inserted into the connector unit and holds an optical fiber that propagates light, and including a ring-shaped flange portion which is provided so as to protrude from the main body in a radial direction and has a diameter smaller than an external diameter of the connector unit, and a fixing member which fixes the holding member to the connector unit. The main body includes a cutout portion which connects to a surface opposite to a surface facing the connector unit and which is partially cut out toward a center of the main body. The flange portion includes a groove portion which connects to the cutout portion and opens to an outer circumferential side, on a surface which faces the fixing member and which is perpendicular to a central axis of the holding member.

A biological optical measurement system according to another aspect of the invention includes a measurement probe configured to be inserted into a subject, and a biological optical measurement apparatus configured to perform an optical measurement on body tissue in the subject through the measurement probe. The biological optical measurement apparatus includes a connector unit to which the measurement probe is detachably connected, a supply unit configured to supply air to the connector unit, a pipe that connects the connector unit and the supply unit, a pressure detection unit configured to detect a pressure value in the pipe, and an abrasion determination unit configured to determine abrasion of the connector unit based on the pressure value detected by the pressure detection unit under conditions that the measurement probe is connected to the connector unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
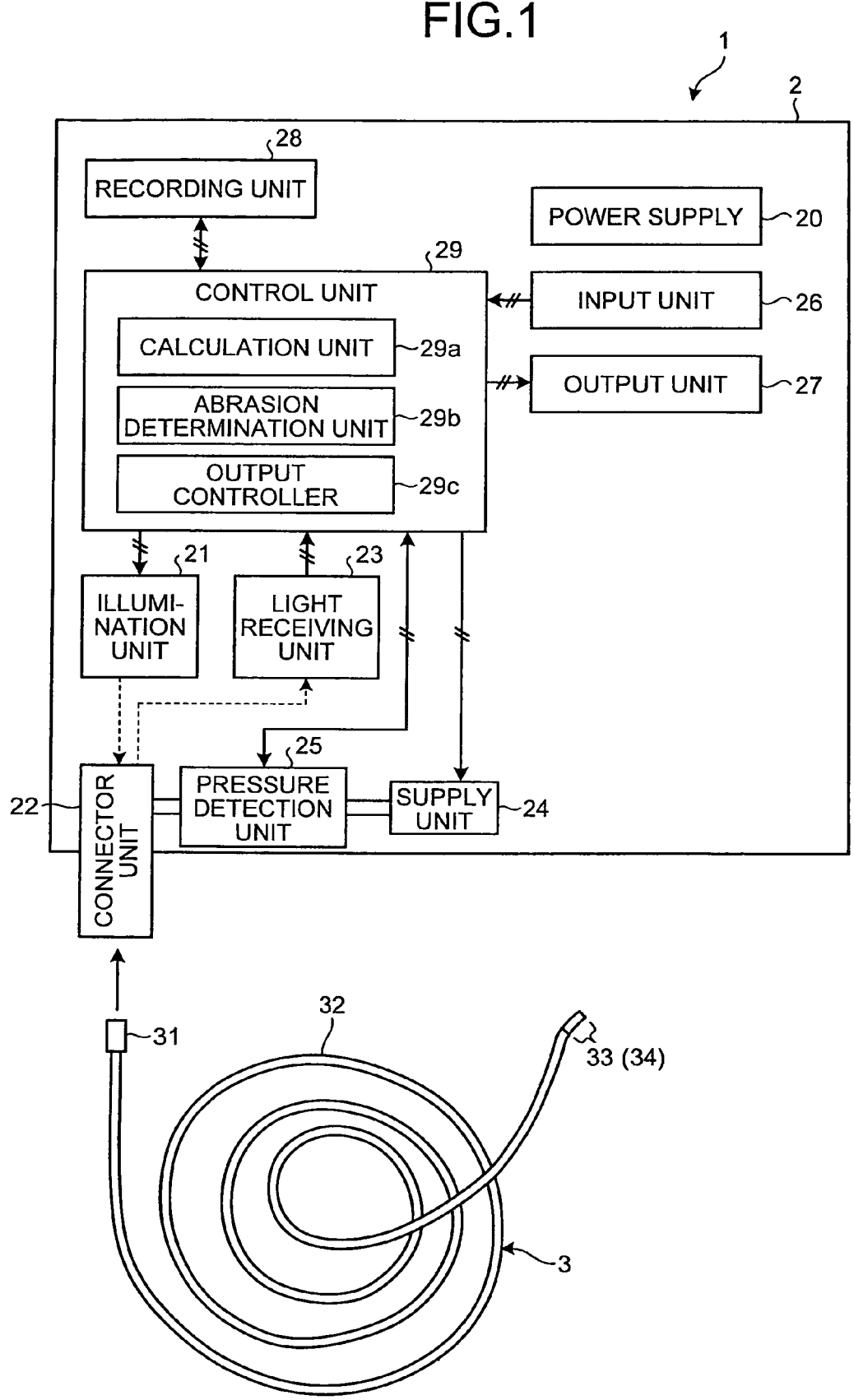
FIG. 1 is a block diagram schematically illustrating a configuration of a biological optical measurement system according to a first embodiment of the present invention.

Hereinafter, modes for carrying out the present invention (hereinafter referred to as "embodiments") will be described with reference to the drawings. In the description of the drawings, the same components are given the same reference numerals. Note that the drawings are schematic and relationships between the thickness and width of each component and ratios between each component are different from the actual values. Further, there may be differences in dimensions and ratios between the drawings. The present invention is not limited by the embodiments.

First Embodiment

FIG. 1 is a block diagram schematically illustrating a configuration of a biological optical measurement system according to a first embodiment of the present invention.

A biological optical measurement system 1 illustrated in FIG. 1 includes a biological optical measurement apparatus 2 which performs optical measurements on an object to be measured such as body tissue that is a scatterer and detects the nature (characteristics) of an object to be measured and a measurement probe 3 which can be attached to and detached from the biological optical measurement apparatus 2 and is inserted into a subject.

First, the biological optical measurement apparatus 2 will be described. The biological optical measurement apparatus 2 includes a power supply 20, an illumination unit 21, a connector unit 22, a light receiving unit 23, a supply unit 24, a pressure detection unit 25, an input unit 26, an output unit 27, a recording unit 28, and a control unit 29. The power supply 20 supplies power to each unit of the biological optical measurement apparatus 2.

The illumination unit 21 irradiates illumination light to an object to be measured through the connector unit 22. The illumination unit 21 is realized by an incoherent optical source such as a white LED (Light Emitting Diode), a xenon lamp, a tungsten lamp, and a halogen lamp and one or a plurality of lenses as needed. Examples of such lenses include a condenser lens and a collimating lens. The illumination unit 21 outputs incoherent light including at least one spectrum component to the measurement probe 3 as the illumination light irradiated to the object to be measured through the connector unit 22.

The connector unit 22 detachably connects the measurement probe 3 to the biological optical measurement apparatus 2. The connector unit 22 is realized by using an SMA connector.

Figure 2:
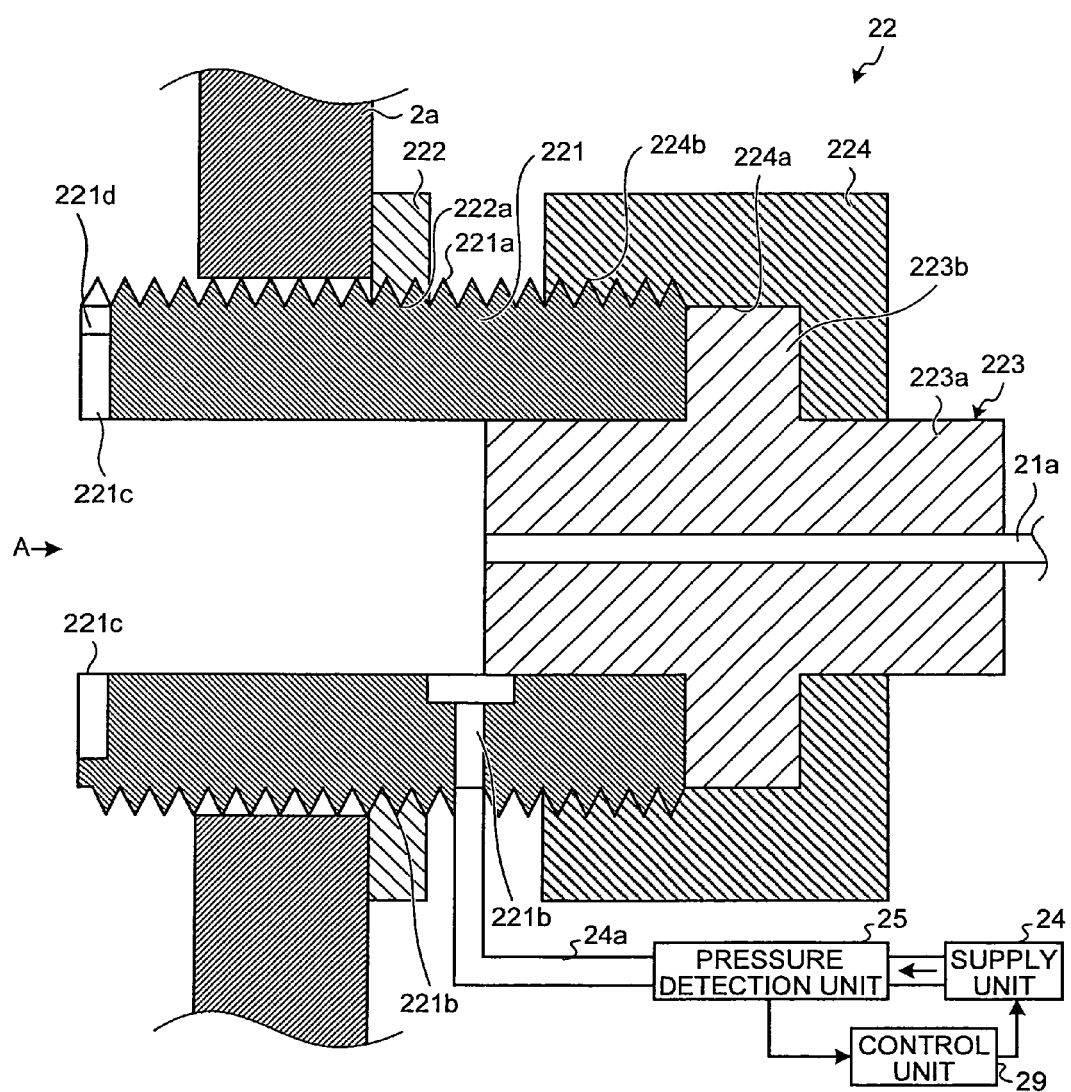
FIG. 2 is a cross-sectional view of a connector unit of a biological optical measurement apparatus of the biological optical measurement system according to the first embodiment of the present invention taken along a central axis of the connector unit.
Figure 3:
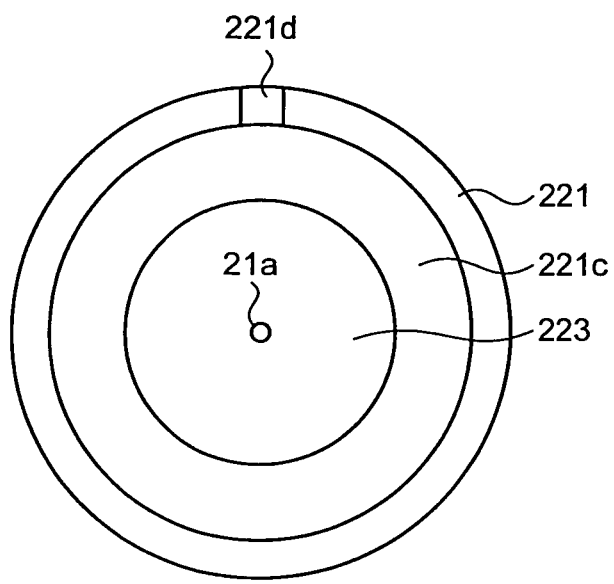
FIG. 3 is a front view of FIG. 2 as seen in an arrow A direction.

Here, a detailed configuration of the connector unit 22 will be described. FIG. 2 is a cross-sectional view of the connector unit 22 taken along a longitudinal direction of the connector unit 22. FIG. 3 is a front view of FIG. 2 as seen in an arrow A direction.

As illustrated in FIGS. 2 and 3, the connector unit 22 includes an adapter member 221 provided to a housing 2a of the biological optical measurement apparatus 2, a first fixing member 222 that fixes the adapter member 221 to the housing 2a, a holding member 223 that can be inserted into the adapter member 221 and holds a plurality of optical fibers 21a, and a second fixing member 224 that fixes the holding member 223 to the adapter member 221.

The adapter member 221 has a cylindrical shape and is formed by using stainless steel or the like. The adapter member 221 is provided so that a part of the adapter member 221 is exposed from the housing 2a of the biological optical measurement apparatus 2. An external thread portion 221a where thread ridges are provided at specified intervals on an outer circumferential surface of the adapter member 221 is formed on the adapter member 221. A through hole 221b that penetrates the adapter member 221 along a radial direction is formed in the adapter member 221. Further, a cutout portion 221c (a spot facing) formed by circularly cutting out a surface of the adapter member 221 facing the measurement probe 3 is formed in the adapter member 221. A groove portion 221d that connects an outer circumferential side of the adapter member 221 and the cutout portion 221c is formed in a part of the outer circumference of the cutout portion 221c (see FIG. 3).

The first fixing member 222 is configured by using a nut or the like. The first fixing member 222 has an internal thread portion 222a that can be screwed with the external thread portion 221a on the inner circumferential side. The first fixing member 222 fixes the adapter member 221 to the housing 2a by screwing the internal thread portion 222a to the external thread portion 221a of the adapter member 221.

The holding member 223 is formed by using ceramic or the like. The holding member 223 includes a cylindrical main body 223a that holds the optical fibers 21a inside the main body 223a and a ring-shaped flange portion 223b provided so as to protrude in a radial direction of the main body 223a. The main body 223a is formed to have substantially the same diameter as the internal diameter of the adapter member 221 so that there is no gap when the main body 223a is inserted into the adapter member 221.

The second fixing member 224 includes an insertion hole 224a which has a C-shaped cross-section and into which the holding member 223 can be inserted. The second fixing member 224 also has an internal thread portion 224b that can be screwed with the external thread portion 221a on a part of the inner circumference of the insertion hole 224a. The second fixing member 224 fixes the holding member 223 to the adapter member 221 by screwing the internal thread portion 224b to the external thread portion 221a of the adapter member 221.

The connector unit 22 configured as described above optically connects the optical fibers 21a of the holding member 223 to the measurement probe 3. Thereby, the connector unit 22 propagates the illumination light emitted from the illumination unit 21 to the measurement probe 3 through the optical fibers 21a of the holding member 223 and propagates return light of the illumination light, which is emitted from the measurement probe 3 and reflected and/or scattered by body tissue, to the light receiving unit 23. In FIG. 2, a cross-section that passes through the central axis of the holding member 223 is used as an example.

Return to FIG. 1, the description of the configuration of the biological optical measurement apparatus 2 will be continued.

The light receiving unit 23 receives and measures return light of the illumination light that is emitted from the measurement probe 3 and reflected and/or scattered by an object to be measured. The light receiving unit 23 is realized by using a plurality of spectroscopic measurement devices, light receiving sensors, or the like. Specifically, in the light receiving unit 23, the spectroscopic measurement devices are provided according to the number of the light receiving fibers in the measurement probe described later. The light receiving unit 23 measures spectrum components and intensity distribution of scattered light emitted from the measurement probe 3 and outputs the measurement result to the control unit 29.

The supply unit 24 supplies air into an interior space of the connector unit 22 under control of the control unit 29. The supply unit 24 is formed by using a pump or the like that sends air. Specifically, the supply unit 24 supplies air into the interior space of the connector unit 22 through a pipe 24a such as a tube and the through hole 221b in the adapter member 221 which function as a supply path in which the air is supplied (see FIG. 2).

The pressure detection unit 25 is provided on the pipe 24a between the connector unit 22 and the supply unit 24. The pressure detection unit 25 detects a pressure value (atmospheric pressure) in the pipe 24a and outputs the measurement result to the control unit 29. The pressure detection unit 25 is realized by using a pressure sensor, an atmospheric pressure sensor, or the like.

The input unit 26 receives an instruction signal that instructs start of the biological optical measurement apparatus 2 or an instruction signal that instructs other various operations and outputs the instruction signal to the control unit 29. The input unit 26 is realized by using push type switches, a touch panel, or the like.

The output unit 27 outputs various information of the biological optical measurement apparatus 2. Specifically, the output unit 27 outputs information indicating that abrasion occurs in the connector unit 22 under control of the control unit 29. The output unit 27 is realized by using a display unit such as a liquid crystal, an organic EL (Electro Luminescence), or the like and a speaker or the like.

The recording unit 28 records various programs for operating the biological optical measurement apparatus 2 and various data and parameters used for optical measurement processing. The recording unit 28 is realized by using a volatile memory, a non-volatile memory, and the like. The recording unit 28 temporarily records information being processed in the biological optical measurement apparatus 2. Further, the recording unit 28 records a measurement result of the subject measured by the biological optical measurement apparatus 2. The recording unit 28 may be formed by using a memory card or the like attached from the outside of the biological optical measurement apparatus 2.

The control unit 29 controls processing operations of each unit of the biological optical measurement apparatus 2. The control unit 29 is configured by using a CPU (Central Processing Unit) or the like and integrally controls the biological optical measurement apparatus 2 by transmitting corresponding instruction information, data, and the like to each unit of the biological optical measurement apparatus 2. The control unit 29 includes a calculation unit 29a, an abrasion determination unit 29b, and an output controller 29c.

The calculation unit 29a performs a plurality of arithmetic processes on the basis of a measurement result measured by the light receiving unit 23 and calculates a characteristic value related to the nature of the object to be measured. For example, a type of the characteristic value is set according to the instruction signal received by the input unit 26.

The abrasion determination unit 29b determines abrasion of the connector unit 22 on the basis of the pressure value detected by the pressure detection unit 25 under the condition that the measurement probe 3 is connected to the connector unit 22. For example, the abrasion determination unit 29b determines whether or not the pressure value inputted from the pressure detection unit 25 is greater than or equal to a specified threshold value and when the pressure value is not greater than or equal to the threshold value, the abrasion determination unit 29b determines that abrasion occurs in the connector unit 22.

When the abrasion determination unit 29b determines that abrasion occurs in the connector unit 22, the output controller 29c causes the output unit 27 to output information indicating that abrasion occurs in the connector unit 22.

Next, the measurement probe 3 will be described. The measurement probe 3 is configured by using at least plurality of optical fibers. Specifically, the measurement probe 3 is realized by using an illumination fiber that emits the illumination light to the object to be measured and a plurality of light receiving fibers into which return light of the illumination light reflected and/or scattered by the object to be measured enters at different angles. The measurement probe 3 includes a proximal end portion 31 detachably connected to the connector unit 22 of the biological optical measurement apparatus 2, a flexible portion 32 having flexibility, and a distal end portion that emits the illumination light supplied from the illumination unit 21 and receives the return light of the illumination light from the object to be measured. A distal end portion 33 is provided with a rod lens 34.

Figure 4:
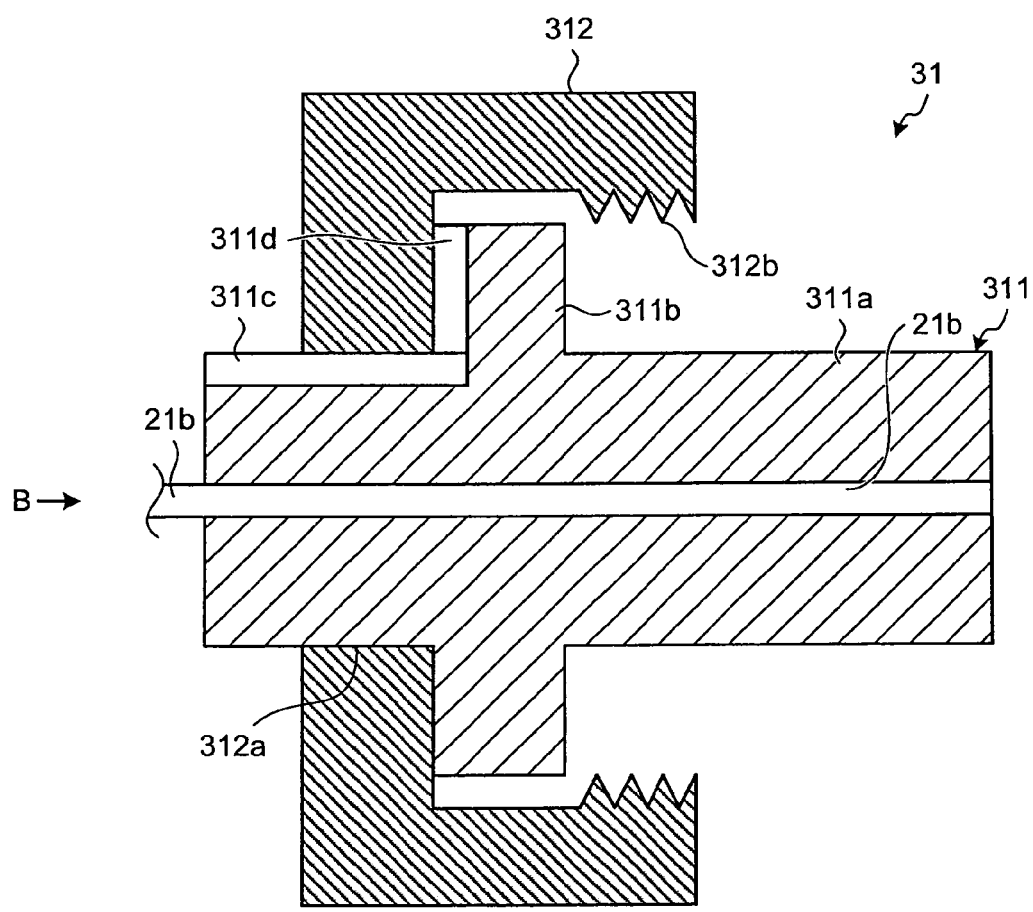
FIG. 4 is a cross-sectional view of a proximal end portion of a measurement probe of the biological optical measurement system according to the first embodiment of the present invention taken along a central axis of the proximal end portion.
Figure 5:
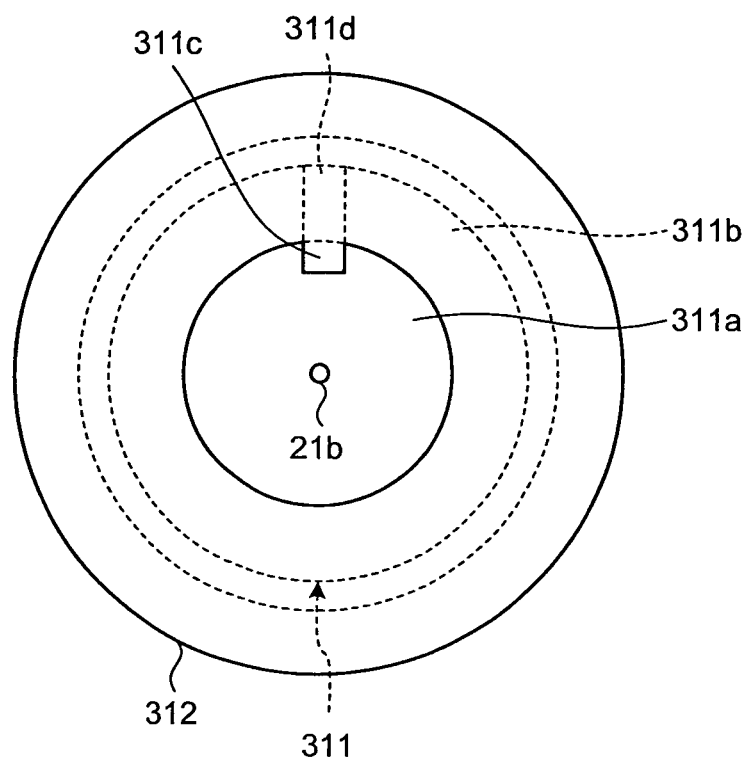
FIG. 5 is a front view of FIG. 4 as seen in an arrow B direction.

Here, a detailed configuration of the proximal end portion 31 of the measurement probe 3 will be described. FIG. 4 is a cross-sectional view of the proximal end portion 31 of the measurement probe 3 taken along a longitudinal direction of the proximal end portion 31. FIG. 5 is a front view of FIG. 4 as seen in an arrow B direction.

As illustrated in FIGS. 4 and 5, the proximal end portion 31 includes a holding member 311 that can be inserted into the adapter member 221 and a fixing member 312 that fixes the holding member 311 to the adapter member 221.

The holding member 311 includes a cylindrical main body 311a that holds optical fibers 21b inside the main body 311a and a ring-shaped flange portion 311b provided so as to protrude in a radial direction of the main body 311a. In the main body 311a, a cutout portion 311c is formed which connects to a surface opposite to a surface facing the connector unit 22 and which is partially cut out toward the center of the main body 311a. The diameter of the flange portion 311b is larger than the inside diameter of the adapter member 221 and smaller than the outside diameter of the adapter member 221. Further, in the flange portion 311b, a groove portion 311d is formed, which connects to the cutout portion 311c and opens to the outer circumferential side, in a surface which faces the fixing member 312 and which is perpendicular to the central axis of the holding member 311.

The fixing member 312 includes an insertion hole 312a which has a C-shaped cross-section and into which the holding member 311 can be inserted. The fixing member 312 also includes an external thread portion 312b, which can be screwed with the external thread portion 221a, on a part of an end portion of the inner circumferential surface. The fixing member 312 fixes the holding member 311 to the adapter member 221 by screwing the external thread portion 312b to the external thread portion 221a of the adapter member 221.

Figure 6:
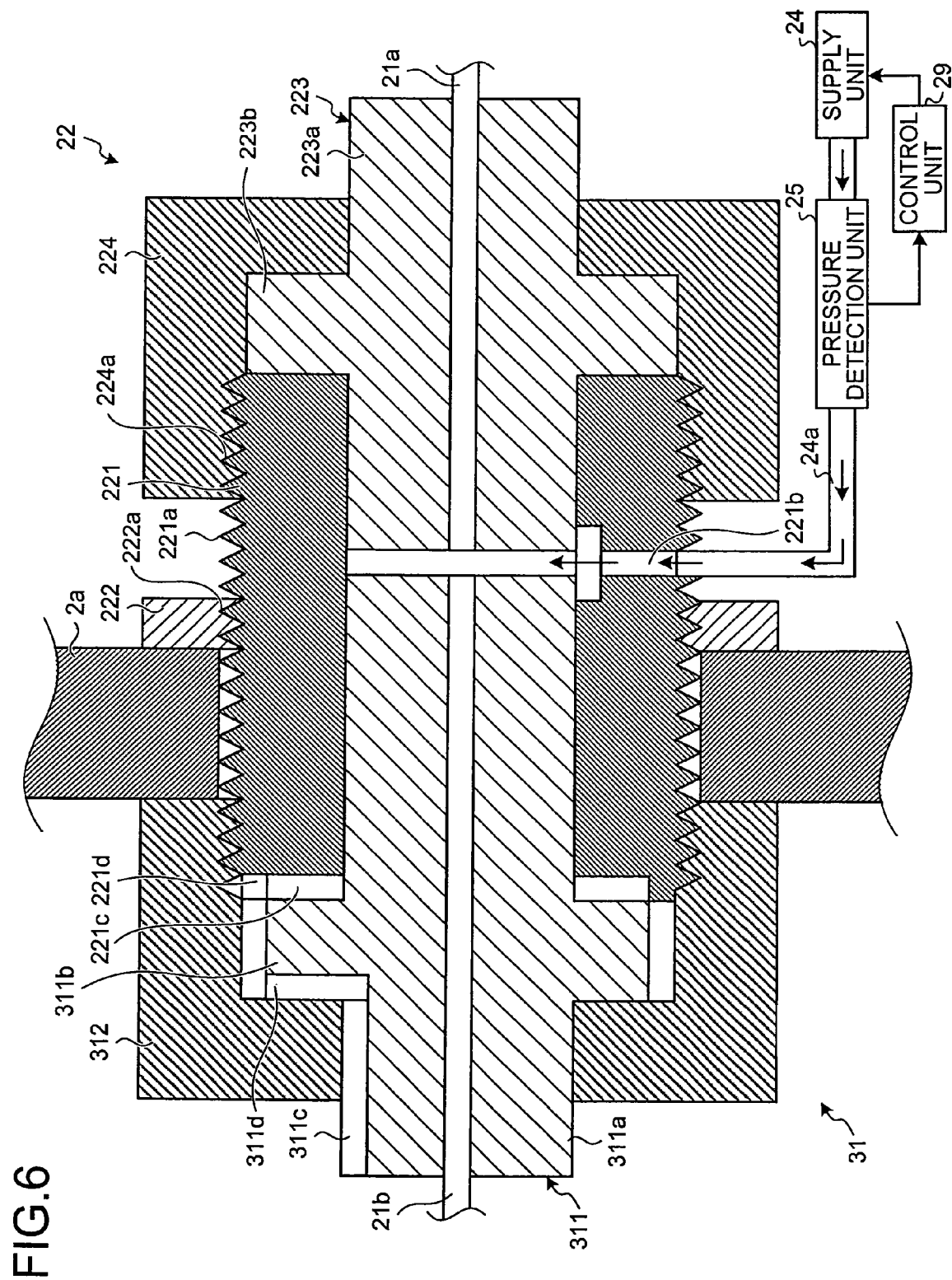
FIG. 6 is a cross-sectional view illustrating a state in which the measurement probe is connected to the biological optical measurement apparatus of the biological optical measurement system according to the first embodiment of the present invention.

As illustrated in FIG. 6, the proximal end portion 31 of the measurement probe 3 configured like this is connected to the connector unit 22 of the biological optical measurement apparatus 2, so that the optical fibers 21a and the optical fibers 21b are optically connected.

Figure 7:
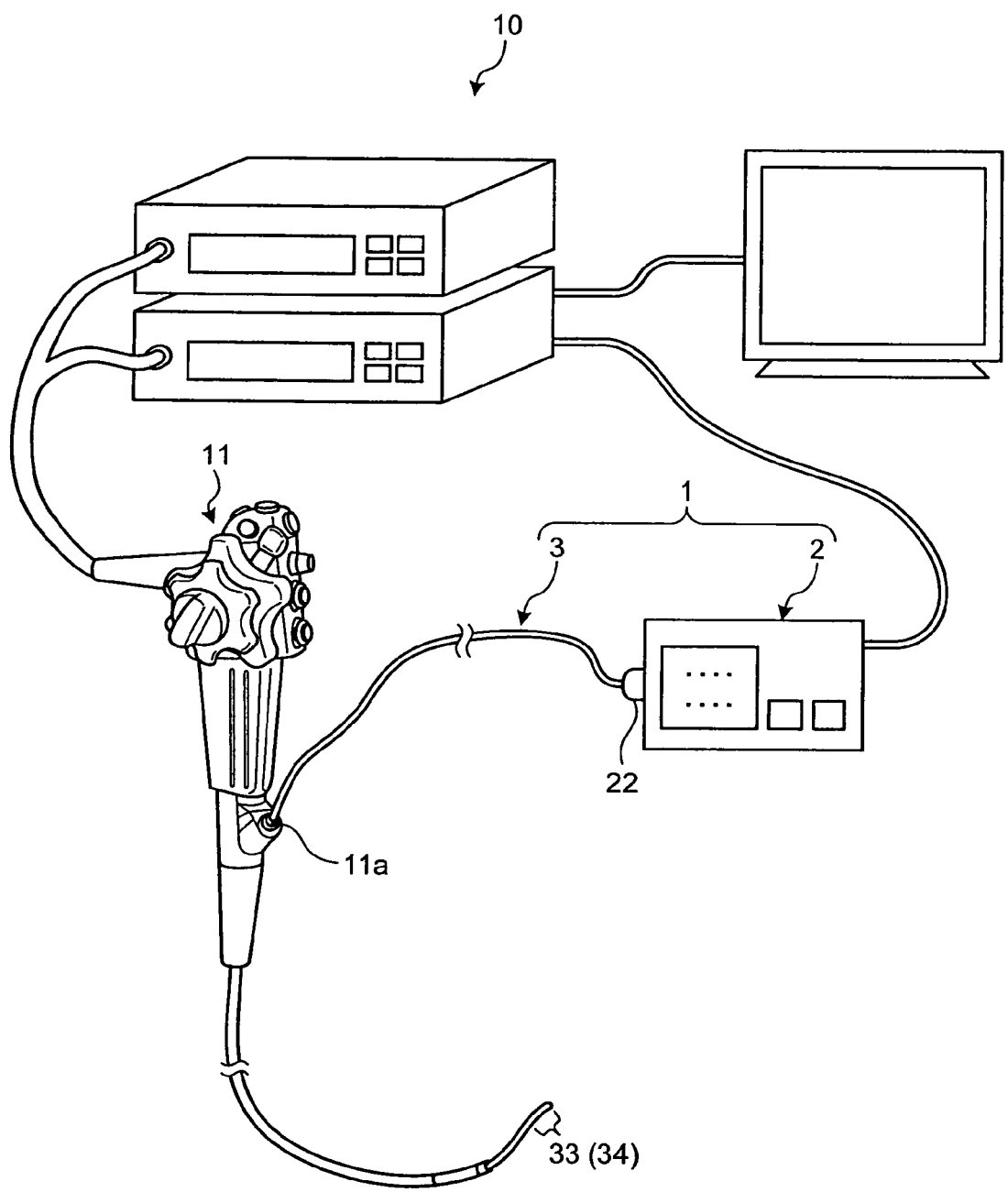
FIG. 7 is a view illustrating a state in which the biological optical measurement system according to the first embodiment is used in an endoscope system.

As illustrated in FIG. 7, in the biological optical measurement system 1 configured as described above, the measurement probe 3 is inserted into the subject through a treatment tool channel 11a provided on an endoscope apparatus 11 (an endoscope scope) of an endoscope system 10, the illumination fiber emits the illumination light to the object to be measured, and the light receiving fibers receives the return light of the illumination light, which is reflected and/or scattered by the object to be measured, at different angles and propagates the return light to the light receiving unit 23 of the biological optical measurement apparatus 2 to emit the return light. Thereafter, the calculation unit 29a calculates a characteristic value of the nature of the object to be measured on the basis of a measurement result of the light receiving unit 23.

Figure 8:
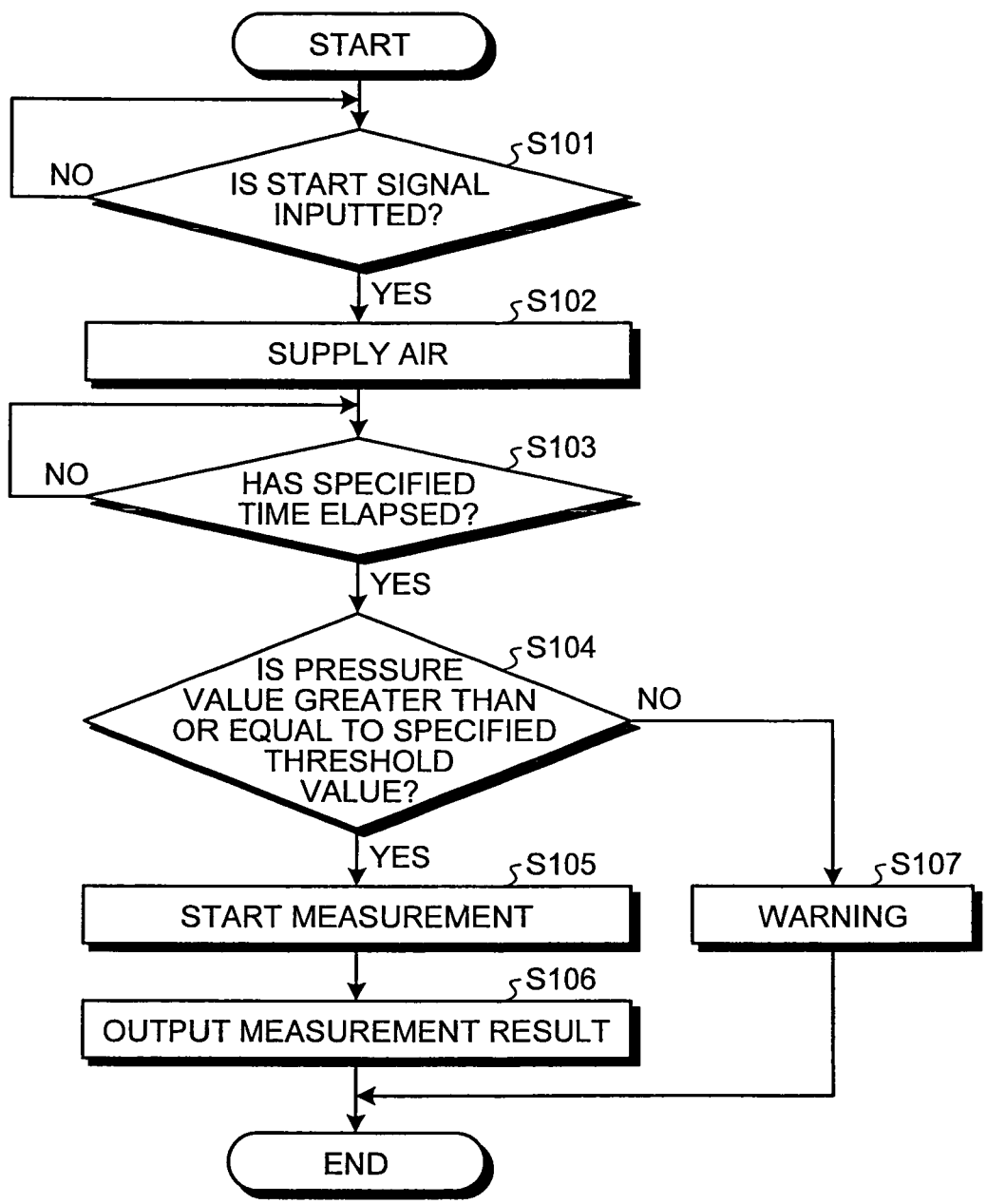
FIG. 8 is a flowchart illustrating an overview of a process performed by the biological optical measurement system of the present invention.

Next, a process performed by the biological optical measurement system 1 will be described. FIG. 8 is a flowchart illustrating an overview of the process performed by the biological optical measurement system 1.

As illustrated in FIG. 8, under the condition that the measurement probe 3 is connected to the biological optical measurement apparatus 2, when a start signal to start a measurement of body tissue is inputted from the input unit 26 (step S101: Yes), the control unit 29 drives the supply unit 24 to supply air into the adapter member 221 (step S102).

Subsequently, the control unit 29 determines whether or not a specified time has elapsed (step S103). When the control unit 29 determines that the specified time has elapsed (step S103: Yes), the biological optical measurement system 1 proceeds to step S104. On the contrary, when the control unit 29 determines that the specified time has not elapsed (step S103: No), the biological optical measurement system 1 continues the process of step S103.

Figure 9:
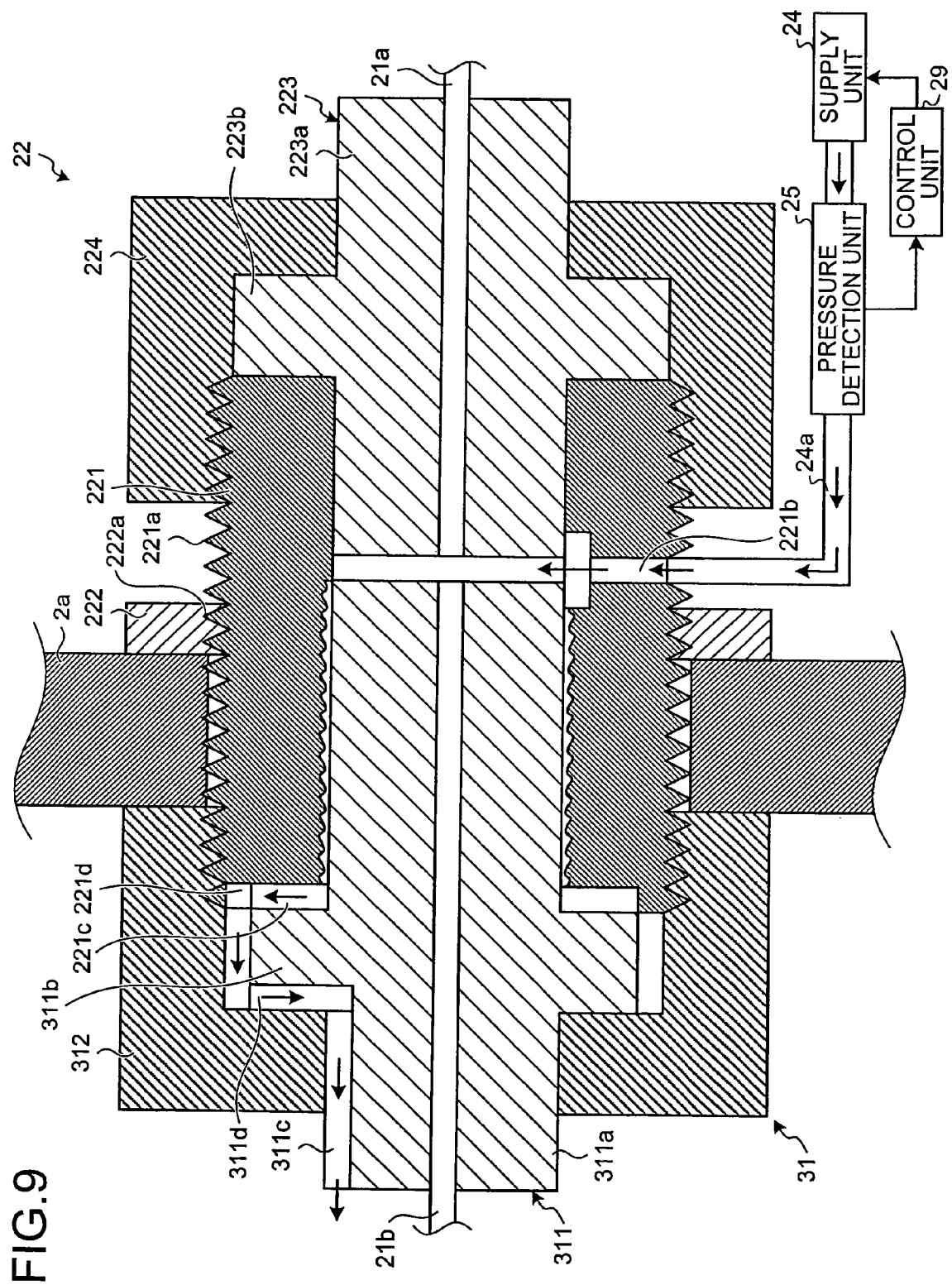
FIG. 9 is a cross-sectional view illustrating a state in which abrasion occurs in the connector unit of the biological optical measurement apparatus according to the first embodiment of the present invention.

In step S104, the abrasion determination unit 29b determines whether or not a pressure value detected by the pressure detection unit 25 is greater than or equal to a specified threshold value. For example, as illustrated in FIG. 9, when abrasion occurs on a surface of the inner circumferential side of the adapter member 221, if a gap generated by the abrasion is connected to the groove portion 311d and the air supplied by the supply unit 24 leaks to the outside, and thus the pressure value in the pipe 24a detected by the pressure detection unit 25 is not greater than or equal to the specified threshold value, the abrasion determination unit 29b determines that abrasion occurs in the connector unit 22. Thereby, a user can reliably know the abrasion generated by use in the connector unit 22. When the abrasion determination unit 29b determines that the pressure value detected by the pressure detection unit 25 is greater than or equal to the specified threshold value (step S104: Yes), the biological optical measurement system 1 starts the measurement of the body tissue (step S105).

Subsequently, the output controller 29c causes the output unit 27 to output a measurement result (step S106). After step S106, the biological optical measurement system 1 ends the process.

In step S104, when the abrasion determination unit 29b determines that the pressure value detected by the pressure detection unit 25 is not greater than or equal to the specified threshold value (step S104: No), the output controller 29c causes the output unit 27 to output a warning indicating that the connector unit 22 is abraded (step S107). After step S107, the biological optical measurement system 1 ends the process.

In step S101, when the start signal to start the measurement of body tissue is not inputted from the input unit 26 (step S101: No) under the condition that the measurement probe 3 is connected to the biological optical measurement apparatus 2, the biological optical measurement system 1 waits till the start signal is inputted.

According to the first embodiment of the present invention described above, under the condition that the measurement probe 3 is connected to the connector unit 22, the abrasion determination unit 29b determines the abrasion of the connector unit 22 on the basis of the pressure value in the pipe 24a detected by the pressure detection unit 25 provided on the pipe 24a between the supply unit 24 that supplies air to the connector unit 22 and the connector unit 22, so that the abrasion of the connector unit 22 can be accurately detected.

Further, according to the first embodiment of the present invention, when the abrasion determination unit 29b determines that abrasion occurs in the connector unit 22, the output controller 29c causes the output unit 27 to output information indicating that abrasion occurs in the connector unit 22. As a result, a user can reliably know the abrasion of the connector unit 22.

In the first embodiment of the present invention, the supply unit 24 supplies air into the connector unit 22. However, for example, it is possible to absorb air in the connector unit 22 and generate a negative pressure in the connector unit 22. In this case, the abrasion determination unit 29b determines whether or not the pressure value detected by the pressure detection unit 25 is smaller than or equal to a specified threshold value, so that the abrasion determination unit 29b may determine whether or not abrasion occurs in the connector unit 22.

Second Embodiment

Next, a second embodiment of the present invention will be described. In the biological optical measurement system according to the second embodiment, the connector unit of the biological optical measurement apparatus and the proximal end portion of the measurement probe are different from those in the first embodiment described above. Therefore, the connector unit of the biological optical measurement apparatus and the proximal end portion of the measurement probe will be described below. The same components as those in the first embodiment described above are given the same reference numerals.

Figure 10:
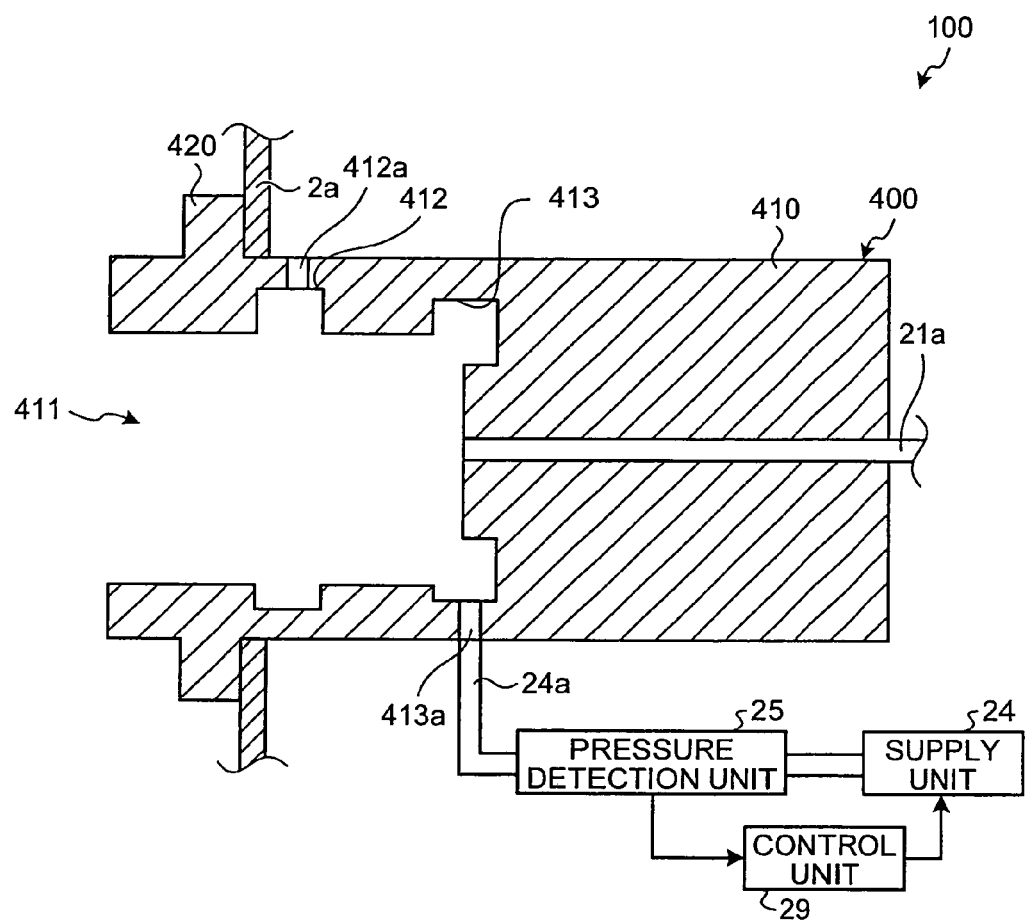
FIG. 10 is a cross-sectional view of a connector unit of a biological optical measurement apparatus of a biological optical measurement system according to a second embodiment of the present invention taken along a central axis of the connector unit.

FIG. 10 is a cross-sectional view of a connector unit 400 of a biological optical measurement apparatus 100 according to the second embodiment of the present invention taken along a central axis of the connector unit 400.

The connector unit 400 illustrated in FIG. 10 includes a cylindrical main body 410 and a ring-shaped flange portion 420 provided so as to protrude in a radial direction of the main body 410.

The main body 410 has a cylindrical shape and holds a plurality of optical fibers 21a. The main body 410 is provided with an insertion hole 411 into which a proximal end portion of a measurement probe 500 described later is inserted. A first groove portion 412 and a second groove portion 413, which are formed by circularly cutting the inside of the insertion hole 411 in the radial direction of the insertion hole 411, are formed in the main body 410. In the first groove portion 412, an exhaust hole 412a is formed which penetrates the main body 410 in the radial direction and exhausts air in the connector unit 400. In the second groove portion 413, a through hole 413a is formed which penetrates the main body 410 in the radial direction and is connected to the supply unit 24 through the pipe 24a.

Figure 11:
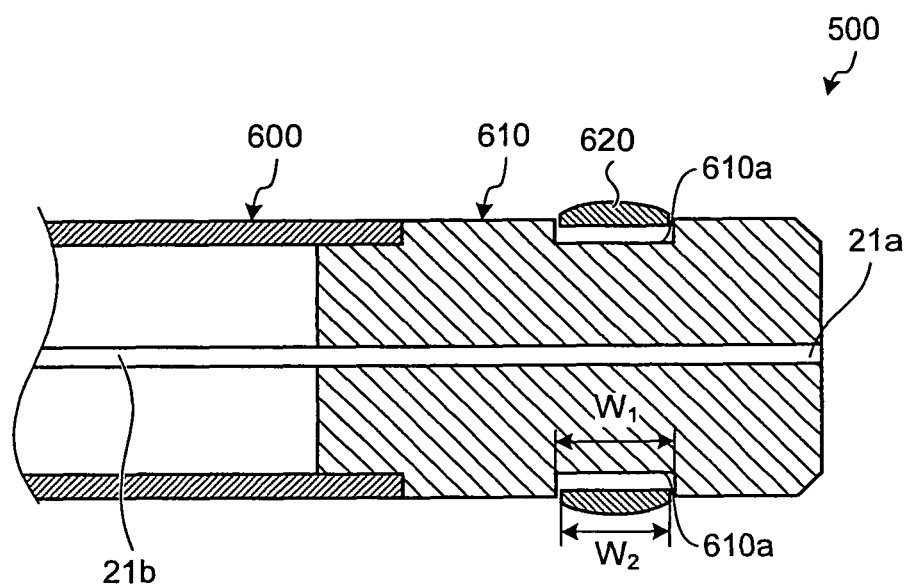
FIG. 11 is a cross-sectional view of a proximal end portion of a measurement probe of the biological optical measurement system according to the second embodiment of the present invention taken along a central axis of the proximal end portion.

Next, a proximal end portion 600 of the measurement probe 500 will be described. FIG. 11 is a cross-sectional view of the proximal end portion 600 of the measurement probe 500 according to the second embodiment of the present invention taken along a central axis of the proximal end portion 600.

The proximal end portion 600 of the measurement probe 500 illustrated in FIG. 11 includes a cylindrical main body 610 and a ring-shaped pressure member 620.

The main body 610 holds the optical fibers 21a. In the main body 610, a groove portion 610a is formed by circularly cutting out the main body 610 toward the center.

The pressure member 620 has a ring shape and is attached to the groove portion 610a of the main body 610. The pressure member 620 is configured by using a ring spring that can be elastically deformed in the radial direction. A height W2 of the pressure member 620 in a direction perpendicular to the diameter of the pressure member 620 is smaller than a groove width W1 of the groove portion 610a.

Figure 12:
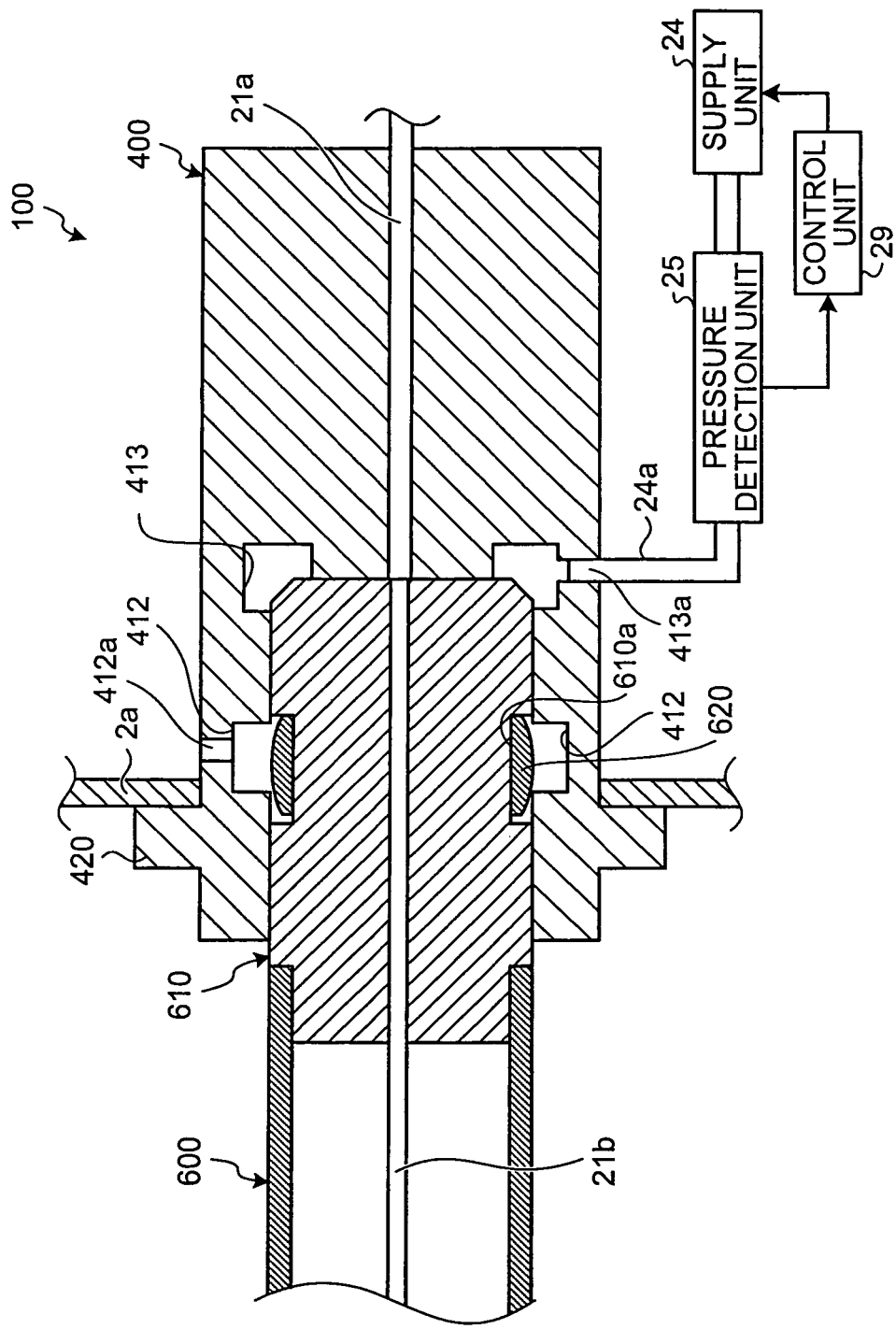
FIG. 12 is a cross-sectional view illustrating a state in which the measurement probe is connected to the biological optical measurement apparatus of the biological optical measurement system according to the second embodiment of the present invention.
Figure 13:
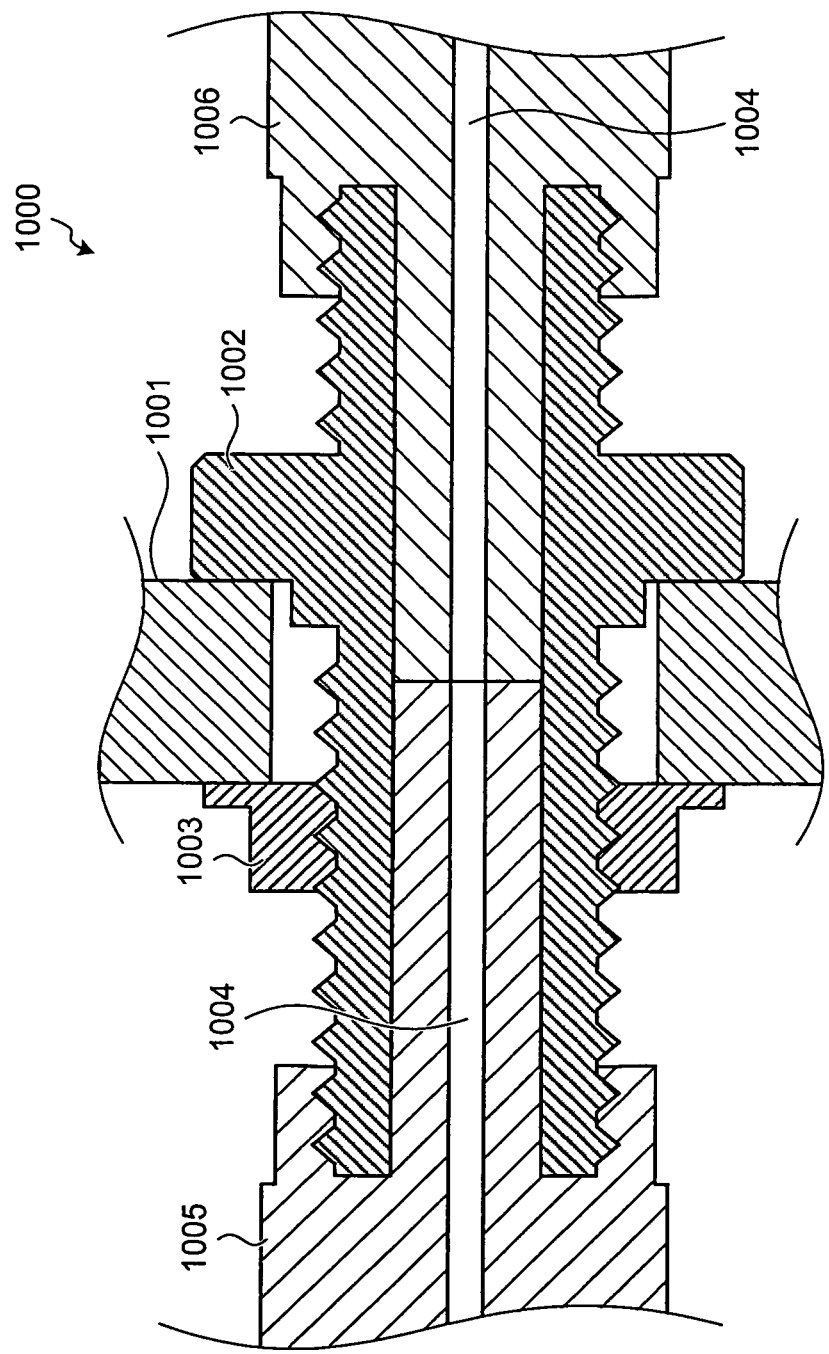
FIG. 13 is a cross-sectional view illustrating a state in which SAM connectors are used as connectors to connect a conventional biological optical measurement apparatus and a measurement probe.

In the biological optical measurement apparatus 100 configured like this, when the proximal end portion 600 of the measurement probe 500 is inserted into the connector unit 400, the proximal end portion 600 is inserted in a state in which the diameter of the pressure member 620 is the same as that of the insertion hole 411 of the connector unit 400 and the pressure member 620 is compressed toward the center. Thereafter, as illustrated in FIG. 12, when the pressure member 620 reaches the first groove portion 412, the pressure member 620 expands in the radial direction. At this time, the pressure member 620 receives a rightward force in FIG. 12 from the connector unit 400 (an effect of an R surface). Thereby, the proximal end portion 600 is fixed to the connector unit 400 so that the proximal end portion 600 is not pulled out from the connector unit 400. At the same time, the proximal end portion 600 is pressed to the connector unit 400, so that connection efficiency is ensured. As a result, a user can connect the measurement probe 500 to the biological optical measurement apparatus 100 by a single operation and optically connect the optical fibers 21a held by the connector unit 400 and the optical fibers 21b of the measurement probe 500.

The control unit 29 causes the supply unit 24 to supply air under the condition that the measurement probe 500 is connected to the connector unit 400. In this case, the abrasion determination unit 29b determines abrasion of the connector unit 400 on the basis of the pressure value detected by the pressure detection unit 25 after a specified time has elapsed. Thereafter, when the abrasion determination unit 29b determines that abrasion occurs in the connector unit 400, the output controller 29c causes the output unit 27 to output information indicating that abrasion occurs in the connector unit 400. Thereby, the user can accurately know the abrasion generated in the connector unit 400.

According to the second embodiment of the present invention described above, it is possible to connect the measurement probe 500 to the connector unit 400 by a single operation, and it is also possible to determine abrasion of the connector unit 400.

Further, according to the second embodiment of the present invention, the configurations of the connector unit 400 and the measurement probe 500 can be simpler than those in the first embodiment described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biological optical measurement apparatus to which a measurement probe configured to be inserted into a subject is connected and which performs an optical measurement on body tissue, the biological optical measurement apparatus comprising:
    a connector unit to which the measurement probe is detachably connected;
    a supply unit configured to supply air to the connector unit;
    a pipe that connects the connector unit and the supply unit;
    a pressure detection unit configured to detect a pressure value in the pipe; and
    an abrasion determination unit configured to determine abrasion of the connector unit based on the pressure value detected by the pressure detection unit under conditions that the measurement probe is connected to the connector unit.

2. The biological optical measurement apparatus according to claim 1,
    wherein the connector unit includes:
    a cylindrical adapter member to which the measurement probe is configured to be inserted;
    a holding member which is configured to be inserted into the adapter member and holds an optical fiber that propagates light; and
    a fixing member which fixes the holding member to the adapter member, and
    wherein the adapter member includes:
    a cutout portion formed by circularly cutting out a surface of the adapter member facing the measurement probe,
    a groove portion which connects an outer circumferential side of the adapter member and the cutout portion, and
    a through hole which connects an inner circumferential side and the outer circumferential side and to which the supply unit is connected through the pipe.

3. The biological optical measurement apparatus according to claim 1, wherein
    the connector unit has a cylindrical shape, holds an optical fiber that propagates light, and includes an insertion hole on a surface facing the measurement probe, the measurement probe being configured to be inserted into the insertion hole, the insertion hole includes a first groove portion and a second groove portion, which are circularly cut out along a longitudinal direction, the first groove portion includes an exhaust hole which penetrates in a radial direction and is configured to exhaust air in the connector unit, and the second groove portion includes a through hole which penetrates in a radial direction and to which the supply unit is connected through the pipe.

4. The biological optical measurement apparatus according to claim 1, further comprising:

an output unit configured to output information indicating that abrasion occurs in the connector unit; and an output controller configured to cause the output unit to output the information indicating that abrasion occurs in the connector unit when the abrasion determination unit determines that abrasion occurs in the connector unit.

5. A measurement probe detachably connected to a connector unit of a biological optical measurement apparatus which performs an optical measurement on body tissue, the measurement probe comprising:

a holding member including a main body which has a cylindrical shape having the same diameter as an internal diameter of the connector unit and which is configured to be inserted into the connector unit and holds an optical fiber that propagates light, and including a ring-shaped flange portion which is provided so as to protrude from the main body in a radial direction and has a diameter smaller than an external diameter of the connector unit; and a fixing member which fixes the holding member to the connector unit, wherein the main body includes a cutout portion which connects to a surface opposite to, a surface facing the connector unit and which is partially cut out toward a center of the main body, and the flange portion includes a groove portion which connects to the cutout portion and opens to an outer circumferential side, on a surface which faces the fixing member and which is perpendicular to a central axis of the holding member.

6. A biological optical measurement system comprising:

a measurement probe configured to be inserted into a subject; and a biological optical measurement apparatus configured to perform an optical measurement on body tissue in the subject through the measurement probe, wherein the biological optical measurement apparatus includes:

a connector unit to which the measurement probe is detachably connected;

a supply unit configured to supply air to the connector unit;

a pipe that connects the connector unit and the supply unit;

a pressure detection unit configured to detect a pressure value in the pipe; and an abrasion determination unit configured to determine abrasion of the connector unit based on the pressure value detected by the pressure detection unit under conditions that the measurement probe is connected to the connector unit.

\* \* \* \* \*